United States Patent
Dafinger et al.

(10) Patent No.: US 7,803,965 B2
(45) Date of Patent: Sep. 28, 2010

(54) METHOD FOR RECOVERY OF ETHYLENE IN A RECIRCULATING GAS PROCESS FOR THE PRODUCTION OF VINYL ACETATE

(75) Inventors: Willibald Dafinger, Röhrnbach (DE); Peter Holl, Emmerting (DE); Wilhelm Kaiser, Burghausen (DE); Jürgen Guba, Burghausen (DE)

(73) Assignee: Wacker Chemie AG, Munich (DE)

( * ) Notice: Subject to any disclaimer, the term of this patent is extended or adjusted under 35 U.S.C. 154(b) by 232 days.

(21) Appl. No.: 10/599,880

(22) PCT Filed: Mar. 31, 2005

(86) PCT No.: PCT/EP2005/003388
§ 371 (c)(1),
(2), (4) Date: Feb. 19, 2007

(87) PCT Pub. No.: WO2005/100296
PCT Pub. Date: Oct. 27, 2005

(65) Prior Publication Data
US 2008/0004467 A1    Jan. 3, 2008

(30) Foreign Application Priority Data
Apr. 15, 2004   (DE) .................. 10 2004 018 284

(51) Int. Cl.
*C07C 67/48*    (2006.01)
(52) U.S. Cl. ............... 560/248; 560/231; 560/245; 560/208; 560/207
(58) Field of Classification Search ........... 560/206, 560/207, 208, 231, 243, 245, 248
See application file for complete search history.

(56) References Cited

U.S. PATENT DOCUMENTS

| | | | | |
|---|---|---|---|---|
| 3,404,177 A | * | 10/1968 | Baba et al. | 560/245 |
| 3,714,237 A | | 1/1973 | Calcagno et al. | |
| 3,715,389 A | * | 2/1973 | Hoch et al. | 560/246 |
| 3,855,280 A | * | 12/1974 | Severs, Jr. | 560/245 |
| 3,862,216 A | * | 1/1975 | Calcagno et al. | 560/243 |
| 3,904,656 A | * | 9/1975 | Broz | 549/538 |
| 4,032,458 A | * | 6/1977 | Cooley et al. | 568/864 |
| 4,818,347 A | * | 4/1989 | Roscher et al. | 203/42 |

(Continued)

FOREIGN PATENT DOCUMENTS

EP   0985657   *  3/2000

(Continued)

OTHER PUBLICATIONS

Ethylene, 2007, Sc-Tech Encyclopedia, Answers.com (Abstract).*

(Continued)

*Primary Examiner*—Rosalynd Keys
*Assistant Examiner*—Yate' K Cutliff
(74) *Attorney, Agent, or Firm*—Brooks Kushman P.C.

(57) ABSTRACT

The efficiency of vinyl acetate production is increased by scrubbing of off gas followed by $CO_2$ absorption. A portion of the off gas containing substantial quantities of ethylene is recycled to the process, whereas another portion is employed in another ethylene consuming reaction. Despite not removing non-reactive gases, selectivity and yield based on ethylene are both increased.

10 Claims, 1 Drawing Sheet

U.S. PATENT DOCUMENTS

| | | | |
|---|---|---|---|
| 5,288,762 A * | 2/1994 | Park et al. | 521/79 |
| 5,705,683 A * | 1/1998 | Lippert et al. | 562/522 |
| 6,663,692 B2 * | 12/2003 | de Poitiers et al. | 95/237 |
| 6,667,409 B2 * | 12/2003 | Shah et al. | 549/532 |
| 2003/0060642 A1 | 3/2003 | Shah et al. | |

FOREIGN PATENT DOCUMENTS

| | | | |
|---|---|---|---|
| EP | 0985657 A1 | 3/2000 | |
| GB | 1264377 A | 2/1972 | |
| WO | WO 01/00559 A1 | 1/2001 | |
| WO | WO 01/90042 A1 | 11/2001 | |

OTHER PUBLICATIONS

Benfield corp., Gas Processing Handbook: Benfield, 1975, (Abstract).*

* cited by examiner

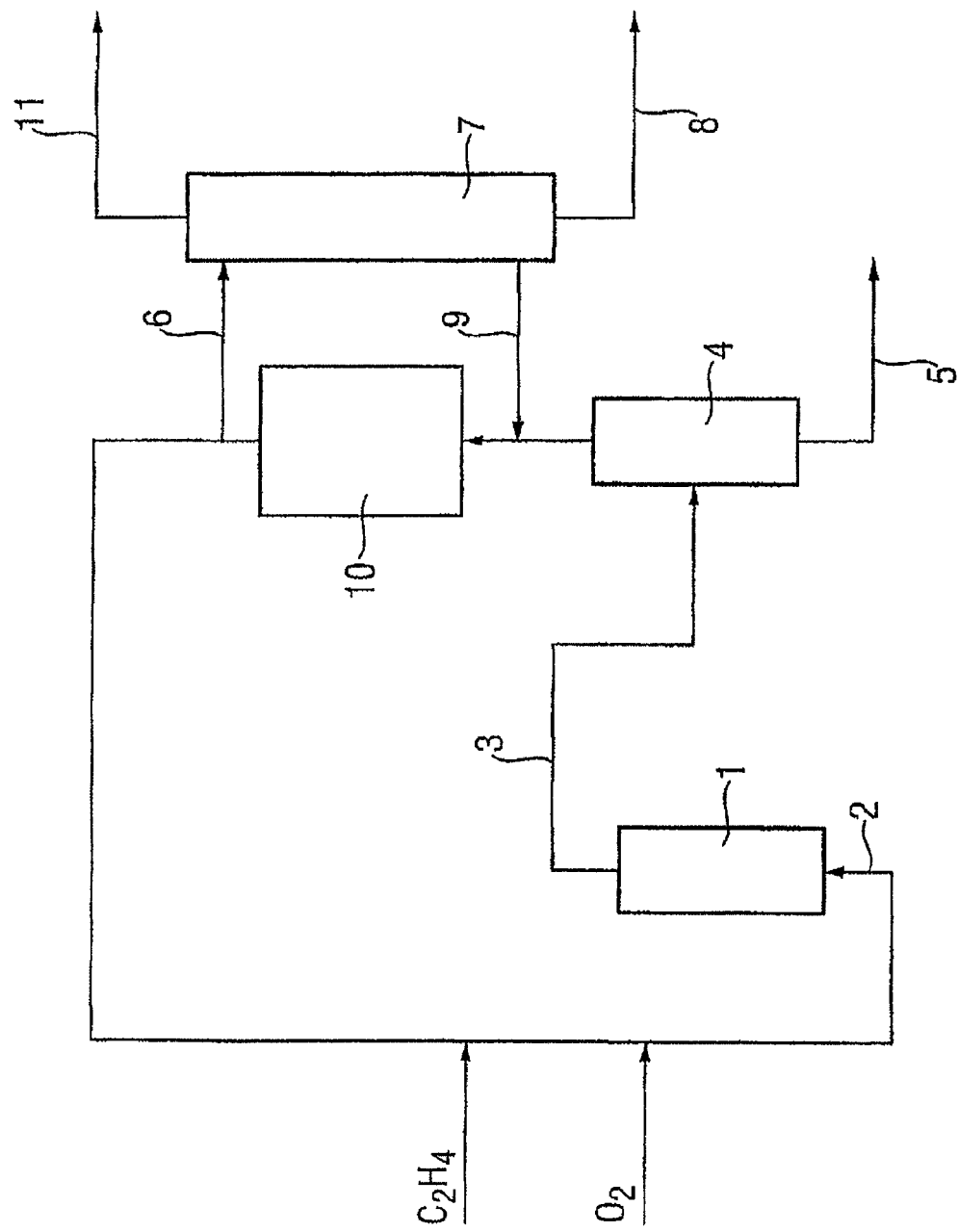

METHOD FOR RECOVERY OF ETHYLENE IN A RECIRCULATING GAS PROCESS FOR THE PRODUCTION OF VINYL ACETATE

CROSS-REFERENCE TO RELATED APPLICATION

This application is the U.S. national phase of PCT Appln. No. PCT/EP2005/003388 filed Mar. 31, 2005, which claims priority to German application 10 2004 018 284.1 filed Apr. 15, 2004.

BACKGROUND OF THE INVENTION

1. Field of the Invention

The invention relates to a process for ethylene recovery in a recirculating gas process for preparing vinyl acetate, in which a substream of the ethylenic product stream is discharged and sent to a process for recovering or converting ethylene.

2. Description of the Related Art

Vinyl acetate is prepared in continuous processes with recycling of the purified product stream. In a heterogeneously catalysed gas phase process, ethylene reacts with acetic acid and oxygen over fixed bed catalysts which generally comprise palladium and alkali metal salts on a support material, and may additionally also be doped with gold, rhodium or cadmium.

The ethylene, oxygen and acetic acid reactants are reacted in an exothermic reaction generally at a pressure of from 8 to 12 bar and a temperature of from 130° C. to 200° C. in a fixed bed tubular reactor to give vinyl acetate:

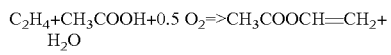

$$C_2H_4 + CH_3COOH + 0.5\ O_2 => CH_3COOCH=CH_2 + H_2O$$

The ethylene conversion is about 10%, the acetic acid conversion from about 20 to 30% and the oxygen conversion up to 90%.

A problem in this reaction is that inert substances are introduced via the ethylene and oxygen reactants, and are difficult to remove, but increasingly reduce the selectivity of the re-action when they are recycled into the reactor and accumulate in the circulating gas. The inerts nitrogen and argon are introduced via the oxygen, and ethane and to a slight extent methane via ethylene. These inerts have to be removed continuously from the system, otherwise their accumulation would inhibit the re-action. Since ethylene constitutes the majority of the recycle gas mixture at from 60 to 70% by volume, the removal of inerts is generally accompanied by a distinct loss of ethylene of from about 1 to 4% by volume of the amount fed. In addition, side reactions form carbon dioxide and further by-products such as methyl acetate and ethyl acetate.

Owing to the incomplete conversion of the reactants, the gaseous product stream is worked up in a continuous process: in a recycle gas scrubber operated with acetic acid, the vinyl acetate target product is washed out of the recycle gas and worked up in subsequent distillation processes. The vinyl acetate-free recycle gas is sent through a gas compressor to the acetic acid saturator and subsequently to the reactor. In order to reduce the $CO_2$ by-product, a portion of the vinyl acetate-free recycle gas is discharged on the pressure side of the recycle gas compressor and sent to a water scrubber. Subsequently, a small fraction is sent to incineration for inerts discharge, and the remainder is passed into a $CO_2$ absorption column and then sent back to gas recirculation in $CO_2$ free form.

The inerts discharged by means of removal of ethylene from the recycle gas prevents accumulation of ethane, methane, argon and nitrogen in the recycle gas stream. The amount of the inert stream discharged is controlled depending on the ethylene concentration in the recycle gas. When the amounts discharged are too small, the inerts become concentrated in the recycle gas and the ethylene concentration in the recycle gas falls. However, the ethylene selectivity increases with the ethylene content of the recycle gas. The higher the ethylene content in the recycle gas, i.e. the more ethylene comprising inerts from the recycle gas is removed and "fresh" ethylene is supplied, the better the ethylene selectivity is. However, from a certain proportion, a more extensive discharge of ethylene comprising inerts is uneconomic, since each additional ton of vinyl acetate monomer has to be paid for with a disproportionately high fraction of discharged ethylene comprising inerts. Since ethylene is expensive, the recovery of ethylene has the highest priority as a cost-lowering measure.

WO-A 01/00559 describes two common alternatives for ethylene recovery in vinyl acetate preparation by means of gas phase reaction of ethylene, acetic acid and oxygen.

Carbon dioxide is removed from the gas stream leaving the reactor which then comprises primarily ethylene, methane, oxygen, nitrogen and argon. At system pressure, the gas stream is passed into an absorption column and washed with vinyl acetate, and a mixture of methane, nitrogen, oxygen and argon is drawn off at the top of the column and sent to incineration. At the bottom of the column, vinyl acetate and ethylene are withdrawn, the gas mixture is decompressed and ethylene is removed from vinyl acetate. The ethylene is subsequently compressed and passed back into the reactor.

Disadvantages in this context are the energy-intensive decompression-compression step, and the fact that the inerts cannot be removed fully, and thus become increasingly enriched and distinctly lower the selectivity of the reaction.

In a further variant, to which WO-A 01/00559 is directed, the majority of the gaseous product stream is contacted at system pressure with acetic acid in an absorption vessel. At the top of the column, methane, nitrogen, oxygen and argon are re-moved, and a mixture of vinyl acetate, acetic acid and ethyl-ene is drawn off at the bottom of the column. This mixture is contacted in a gas scrubber with the remaining fraction of the gaseous product stream. The ethylene is drawn off at the top and recycled into the reactor; the vinyl acetate is obtained at the bottom of the column and sent to further workup. The decompression/compression step becomes unnecessary, but here too the inert gases accumulate increasingly in the recycle gas.

A similar process is the subject matter of U.S. Pat. No. 3,714,237, in which the gaseous stream is likewise worked up by scrubbing with acetic acid, vinyl acetate is removed, and the residual gas is recycled into the reactor after the carbon dioxide has been washed out. Here too, the inert gases accumulate increasingly in the recycle gas.

SUMMARY OF THE INVENTION

It is therefore an object of the present invention to configure the recycle gas process in the preparation of vinyl acetate in such a way that the accumulation of the inert gases mentioned is very substantially prevented. These and other objects are achieved by a process in which the product gas stream is fed at system pressure to a scrubber and scrubbed with acetic acid, vinyl acetate is removed, the vinyl acetate-free gas is freed of $CO_2$, a portion of the ethylene-containing gas is recycled, and the remainder of the ethylene-containing stream is used in other processes.

BRIEF DESCRIPTION OF THE DRAWINGS

The single drawing figure illustrates a block diagram of one embodiment of the present invention.

DETAILED DESCRIPTION OF THE PREFERRED EMBODIMENTS

The invention thus provides a process for ethylene recovery in a recycle gas process for preparing vinyl acetate by means of a) heterogeneously catalysed reaction of ethylene, acetic acid and oxygen at a pressure of from 1 to 50 bar and a temperature of from 50° C. to 200° C., b) separation of the product gas stream comprising substantially ethylene, vinyl acetate, acetic acid, water, carbon dIoxide and further inert gases, and c) recycling of ethylene into the recycle gas process, characterized in that d) the product gas stream is fed at system pressure to a recycle gas scrubber charged with acetic acid, and vinyl acetate is removed from the recycle gas, and e) the vinyl acetate-free recycle gas is subsequently fed to a $CO_2$ absorption to remove carbon dioxide, and then f) a portion of the ethylenic recycle gas stream is recycled into the reaction system, and the remainder of the ethylenic gas stream is discharged and reused in processes for recovering or converting ethylene.

In the continuous preparation of vinyl acetate, operation is effected in tubular reactors which are charged with a fixed bed catalyst. These catalysts are generally supported catalysts doped with noble metals (or noble metal salts) and promoters, for example bentonite spheres doped with palladium and with gold (cadmium) and potassium salts. The reactor is charged with ethylene, oxygen and acetic acid, and the reaction is carried out preferably at a pressure of from 8 to 12 bar and a temperature of from 130° C. to 200° C. The product gas stream leaving the reactor comprises substantially vinyl acetate, ethylene, acetic acid, water, oxygen, $CO_2$ and the inerts nitrogen, argon, methane and ethane.

The product gas stream is subsequently separated in a recycle gas scrubber operated with acetic acid, in which vinyl acetate, acetic acid, water and further condensable fractions are removed, and the vinyl acetate monomer is obtained by means of distillative workup. After the removal of the condensable fractions (vinyl acetate, acetic acid, water), the recycle gas typically has the following composition:

from 60 to 65% by volume of ethylene,
from 12 to 18% by volume of $CO_2$,
from 5 to 8% by volume of ethane,
from 4 to 9% by volume of oxygen,
from 4 to 6% by volume of nitrogen,
from 1 to 2% by volume of argon,
from 0.5 to 1% by volume of methane.

This composition makes clear that, to effectively remove methane, ethane, argon and nitrogen, a relatively high proportion has to be sent to incineration, with a correspondingly high ethylene loss.

In the inventive procedure, the recycle gas is now conducted into a $CO_2$ absorption/desorption, customarily operated with aqueous potassium carbonate solution. After the $CO_2$ scrubbing, the recycle gas generally has the following composition:

from 80 to 83% by volume of ethylene,
from 1 to 4% by volume of $CO_2$,
from 2 to 4% by volume of ethane,
from 3 to 5% by volume of oxygen,
from 3 to 4% by volume of nitrogen,
from 0.5 to 1% by volume of argon,
from 0.2 to 0.4% by volume of methane.

After the $CO_2$ scrubbing, the product stream is divided. A majority of the ethylenic recyle gas stream is recycled into the reactor via a recycle gas compressor and acetic acid saturator. The remainder of the ethylenic gas stream is discharged and reused in processes for converting ethylene. Preference is given to discharging from 1 to 25% by volume, more preferably from 5 to 20% by volume, of the ethylenic gas stream. The carbon dioxide laden with traces of hydrocarbons is passed to thermal disposal.

The recycling is effected preferably into processes for converting ethylene. Examples thereof are oxidation processes for preparing acetaldehyde and for preparing acetic acid, the oxychlorination of ethylene for preparing dichloroethane and the direct chlorination of ethylene to dichloroethane. Further examples are the preparation of ethylene oxide and ethylene glycol, alkylation of benzene to ethylbenzene and optionally de-hydrogenation to styrene, the carbonylation to acrylic acid, the polymerization to polyethylene, the hydroformylation to propionaldehyde, the Reppe carbonylation to propionic acid, and the Alfol process for preparing long-chain, primary alcohols. The ethylene may also be used for recycling in processes for refining hydrocarbons.

With the process according to the invention, the inerts discharge is no longer inevitably associated with the incineration of the valuable ethylene raw material. Virtually 100% utilization of the ethylene is possible; typically, 2% of the ethylene used is lost as a result of the inerts discharge. The generation of environmentally polluting carbon dioxide owing to ethylene incineration is prevented. This corresponds to a drop of 50 kg of $CO_2$ per metric ton of vinyl acetate monomer.

The examples which follow serve to further illustrate the invention:

FIG. 1 shows a simplified diagram of the process:

Example 1:

A 25 m³ tubular reactor 1 which was equipped with a Pd/Au sup-ported catalyst was charged at a pressure of 8.5 bar and a temperature of 160° C. via line 2 with a gas mixture having a gas hourly space velocity (GHSV) of 3500 $h^{-1}$. The gas mixture (recycle gas) had the following composition:

61.7% by volume of ethylene,
10.8% by volume of $CO_2$,
12.7% by volume of acetic acid,
3.4% by volume of ethane,
8.0% by volume of oxygen,
0.8% by volume of nitrogen,
0.8% by volume of argon,
1.0% by volume of methane
0.8% by volume of water.

The recycle gas leaving the reactor 1 was fed via line 3 to a vinyl acetate scrubber 4 operated with acetic acid, and subsequently via line 6 to a carbon dioxide scrubber 7 operated with potash. A vinyl acetate/acetic acid/water mixture was withdrawn via line 5 from the vinyl acetate scrubber 4 and sent to further processing. After the carbon dioxide scrubbing, 200 kg/h, corresponding to approx. 7% by volume, of the recycle gas going to the $CO_2$ removal were passed via line 8 into the acetic acid preparation for ethylene recovery, and the remainder was recycled via line 9 and the recycle gas compressor 10 into the reactor 1. The $CO_2$ discharge for thermal disposal was effected via path 11.

Under these conditions, the catalyst exhibited a space-time yield of 650 g/l·h at an ethylene selectivity of 91.5%.

Example 2:

The procedure was analogous to Example 1, with the difference that, after the $CO_2$ scrubbing, 300 kg/h, i.e. approx. 10% by volume, of the recycle gas going to the $CO_2$ removal, is discharged. This increased the ethylene content in the recycle gas to 64% by volume; the other components were adjusted correspondingly. The reaction conditions (GHSV, recycle gas pressure, etc.) remained the same.

The increase in the amount discharged resulted in an increase in the space-time yield to 660 g/l·h with an improvement in the ethylene selectivity to 92.5%, which corresponds to an at least 0.5% increase in the vinyl acetate production.

Example 3:

The procedure was analogous to Example 1, with the difference that, after the $CO_2$ scrubbing, 450 kg/h, i.e. approx. 15% by volume, of the recycle gas going to the $CO_2$ removal is passed into the acetic acid preparation for ethylene recovery. This resulted in an increase in the ethylene content in the recycle gas to 66% by volume; the other components were adjusted correspondingly. The reaction conditions (GHSV, recycle gas pressure, etc.) remained the same.

The increase in the amount discharged resulted in an increase in the ethylene selectivity to 93.0%, which corresponds to a 1% increase in the vinyl acetate production.

The invention claimed is:

1. A process for ethylene recovery in a recirculating gas process for preparing vinyl acetate, comprising:
    a) reacting ethylene, acetic acid and oxygen in a heterogeneously catalyzed reaction at a pressure of from 1 to 50 bar and a temperature of from 50° C. to 200° C. in a reactor,
    b) separating a product gas stream comprising ethylene, vinyl acetate, acetic acid, water, carbon dioxide and non-reactive gases, and
    c) recycling only a portion of ethylene back into the reactor, wherein
    d) the product gas stream is fed from the reactor at system pressure directly to a recycle gas scrubber charged with acetic acid, and vinyl acetate is removed to form a vinyl acetate-free recycle gas, and
    e) the vinyl acetate-free recycle gas is subsequently fed to a $CO_2$ absorption to remove carbon dioxide to form an ethylenic gas stream, and then
    f) a portion of the ethylenic gas stream is recycled into the reactor without further non-reactive gases being separated; and 1% to 25% by volume of the ethylenic gas stream is discharged without further non-reactive gases being separated, and is reused in one or more processes which consume ethylene, other than processes for preparing vinyl acetate.

2. The process of claim 1, wherein the discharged proportion of the ethylenic gas stream is fed to an oxidation processes for preparing ethylene oxide, ethylene glycol, acetaldehyde, or acetic acid, or fed to an oxychlorination of ethylene to dichloroethane, or to a direct chlorination of ethylene to dichloroethane.

3. The process of claim 1, wherein the discharged proportion of the ethylenic gas stream is fed to a process for alkylating benzene to ethylbenzene, a process for carbonylation to acrylic acid, to a polyolefin polymerization, to a hydroformylation process to produce propionaldehyde, in the Reppe carbonylation to propionic acid, or to an Alfol process for preparing long-chain primary alcohols.

4. The process of claim 1, wherein step a) is conducted at a pressure in the range of 8 to 12 bar and at a temperature in the range of 130° C. to 200° C.

5. The process of claim 1, wherein the vinyl acetate-free product gas contains 60 to 65 weight percent ethylene and 12 to 18 weight percent carbon dioxide, and after $CO_2$ removal, contains 80 to 83% ethylene and 1 to 4% $CO_2$.

6. The process of claim 1, wherein 80 to 95% of the ethylenic cycle gas stream is recycled and 5 to 20% is fed to another process consuming ethylene.

7. A process for ethylene recovery in a recirculating gas process for preparing vinyl acetate, comprising:
    a) reacting ethylene, acetic acid and oxygen in a heterogeneously catalyzed reaction in a reactor at a pressure of from 1 to 50 bar and a temperature of from 50° C. to 200° C.,
    b) separating a product gas stream comprising ethylene, vinyl acetate, acetic acid, water, carbon dioxide and non-reactive gases, and
    c) recycling only a portion of ethylene back into the recirculating gas process, wherein
    d) the product gas stream is fed at system pressure to a recycle gas scrubber charged with acetic acid, and vinyl acetate is removed from the recycle gas, and
    e) the vinyl acetate-free recycle gas is subsequently fed to a $CO_2$ absorption to remove carbon dioxide, and then
    f) a portion of the ethylenic recycle gas stream is recycled into the reaction system, without further non-reactive gases being separated; and 1% to 25% by volume of the ethylenic gas stream is discharged without further non-reactive gases being separated, and is reused in one or more processes which consume ethylene, other than processes for preparing vinyl acetate,
wherein the product gas stream separated from the reactor in step b) comprises:
    from 60 to 65% by volume of ethylene,
    from 12 to 18% by volume of CO2,
    from 5 to 8% by volume of ethane,
    from 4 to 9% by volume of oxygen,
    from 4 to 6% by volume of nitrogen,
    from 1 to 2% by volume of argon, and
    from 0.5 to 1% by volume of methane.

8. A process for ethylene recovery in a recirculating gas process for preparing vinyl acetate, comprising:
    a) reacting ethylene, acetic acid and oxygen in a reactor in a heterogeneously catalyzed reaction at a pressure of from 1 to 50 bar and a temperature of from 50° C. to 200° C.,
    b) separating a product gas stream comprising ethylene, vinyl acetate, acetic acid, water, carbon dioxide and non-reactive gases, and
    c) recycling only a portion of ethylene back into the recirculating gas process, wherein
    d) the product gas stream is fed at system pressure to a recycle gas scrubber charged with acetic acid, and vinyl acetate is removed from the recycle gas, and
    e) the vinyl acetate-free recycle gas is subsequently fed to a $CO_2$ absorption to remove carbon dioxide, and then
    f) a portion of the ethylenic recycle gas stream is recycled into the reaction system, without further non-reactive gases being separated; and 1% to 25% by volume of the ethylenic gas stream is discharged without further non-reactive gases being separated, and is reused in one or more processes which consume ethylene, other than processes for preparing vinyl acetate, wherein the ethylene recycle stream, following treatment to remove carbon dioxide in step e), comprises:
- from 80 to 83% by volume of ethylene,
- from 1 to 4% by volume of CO2,
- from 2 to 4% by volume of ethane,
- from 3 to 5% by volume of oxygen,
- from 3 to 4% by volume of nitrogen,
- from 0.5 to 1% by volume of argon, and
- from 0.2 to 0.4% by volume of methane.

9. The process of claim 7, wherein the ethylene recycle stream, following treatment to remove carbon dioxide in step e), comprises:
- from 80 to 83% by volume of ethylene,
- from 1 to 4% by volume of CO2,
- from 2 to 4% by volume of ethane,
- from 3 to 5% by volume of oxygen,
- from 3 to 4% by volume of nitrogen,
- from 0.5 to 1% by volume of argon, and
- from 0.2 to 0.4% by volume of methane.

10. The process of claim 7, wherein a portion of 1 - 25% by weight of ethylene-containing gas from the recycle gas scrubber in step d) is fed to a plant for the production of acetic acid from ethylene.

* * * * *